United States Patent
Staats (10) Patent No.: US 10,591,451 B2
(45) Date of Patent: Mar. 17, 2020

(54) DEVICES AND METHODS FOR LIQUID SAMPLE INJECTION FOR MASS SPECTROMETRY WITH IMPROVED UTILITIES

(71) Applicant: Phoenix S&T, Inc., Chadds Ford, PA (US)

(72) Inventor: Sau Lan Tang Staats, Hockessin, DE (US)

(73) Assignee: PHOENIX S&T, INC., Chadds Ford, PA (US)

(*) Notice: Subject to any disclaimer, the term of this patent is extended or adjusted under 35 U.S.C. 154(b) by 0 days.

(21) Appl. No.: 15/996,127

(22) Filed: Jun. 1, 2018

(65) Prior Publication Data

US 2018/0348179 A1 Dec. 6, 2018

Related U.S. Application Data

(60) Provisional application No. 62/522,269, filed on Jun. 20, 2017, provisional application No. 62/513,785, filed on Jun. 1, 2017.

(51) Int. Cl.
| | |
|---|---|
| G01N 30/72 | (2006.01) |
| H01J 49/04 | (2006.01) |
| H01J 49/16 | (2006.01) |
| G01N 30/60 | (2006.01) |
| C25D 1/02 | (2006.01) |
| C22C 19/00 | (2006.01) |
| C22C 19/05 | (2006.01) |

(52) U.S. Cl.
CPC ........ *G01N 30/7266* (2013.01); *C22C 19/002* (2013.01); *C22C 19/05* (2013.01); *C25D 1/02* (2013.01); *G01N 30/6004* (2013.01); *G01N 30/6078* (2013.01); *H01J 49/0445* (2013.01); *H01J 49/165* (2013.01); *H01J 49/167* (2013.01); *G01N 2030/6013* (2013.01)

(58) Field of Classification Search
CPC .......... G01N 30/7266; G01N 30/6004; G01N 30/6078; G01N 2030/6013; C22C 19/002; C22C 19/05; C25D 1/02; H01J 49/0445; H01J 49/165; H01J 49/167
USPC ........................................ 250/281, 282, 288
See application file for complete search history.

(56) References Cited

U.S. PATENT DOCUMENTS

| | | | |
|---|---|---|---|
| 6,670,607 B2 * | 12/2003 | Wood | G01N 30/7266 106/162.51 |
| 2002/0003209 A1 | 1/2002 | Wood et al. | |
| 2004/0206902 A1 | 10/2004 | Staats | |
| 2005/0121470 A1 * | 6/2005 | Bango | D01D 5/0069 222/187 |

(Continued)

*Primary Examiner* — Nicole M Ippolito
(74) *Attorney, Agent, or Firm* — Leason Ellis LLP (57) ABSTRACT

A new electrospray emitter capable of cone-jet mode spray for liquid flow-rates from sub-microliter/minute to 10's of microliters/minute is provided. The high efficiency of ionization and vaporization enabled by the disclosed spray emitter provides improved sensitivity for mass spectrometer detection. The disclosed spray emitter sprays consistently and robustly a liquid buffer having a large range of compositions of aqueous and organic solvents, and is not sensitive to the polarity of the electric field used to induce spray. The fluidic channel leading to the spray emitter opening does not have an internal taper rendering the spray emitter clog-resistant.

20 Claims, 8 Drawing Sheets

(56) References Cited

U.S. PATENT DOCUMENTS

| | | |
|---|---|---|
| 2006/0022131 A1* | 2/2006 | Tojo .................. G01N 30/7266 250/288 |
| 2006/0208186 A1 | 9/2006 | Goodley et al. |
| 2007/0267293 A1 | 11/2007 | Finch et al. |
| 2008/0265153 A1* | 10/2008 | Zare ........................ C23C 18/44 250/288 |
| 2009/0095057 A1 | 4/2009 | Staats |
| 2009/0283671 A1 | 11/2009 | Oleschuk |
| 2017/0125228 A1* | 5/2017 | Bango ................. H01J 49/0445 |
| 2018/0012746 A1* | 1/2018 | Ouyang .............. H01J 49/0409 |

* cited by examiner

DEVICES AND METHODS FOR LIQUID SAMPLE INJECTION FOR MASS SPECTROMETRY WITH IMPROVED UTILITIES

CROSS-REFERENCE TO RELATED PATENT APPLICATIONS

This application is based on and claims priority to U.S. Provisional Patent Application 62/513,785, filed Jun. 1, 2017 and U.S. Provisional Patent Application 62/522,269, filed Jun. 20, 2017, all of which are incorporated by reference, as if expressly set forth in their respective entireties herein.

TECHNICAL FIELD

The present application relates to devices and methods that improve the performance of nanoliter to tens of microliters per minute flow-rates liquid phase sample injection mass spectrometry and high-performance liquid chromatography-mass spectrometry (LC-MS).

BACKGROUND

Electrospray ionization (ESI) is the predominant technique for vaporizing and ionizing a liquid-phase sample containing molecular species to be input into a mass spectrometer for mass measurements. It has the advantage of being a "soft" ionization technique which creates ions of the intact molecules with minimal molecular fragmentations. In electrospray ionization, the molecules carried in a liquid buffer are pumped through a small tube or capillary toward the inlet region of a mass spectrometer. The opening of the tube, which may be of a variety of designs, called the spray emitter, is placed in close proximity, from under a millimeter to a few centimeters, of the mass spectrometer inlet. The liquid buffer and the molecules it carries vaporize and ionize under a sufficiently large electric field created by a voltage difference from about one to about five kilovolts between the spray emitter and the mass spectrometer inlet. The charged ions in the sprayed eluates, materials that elute from the spray emitter, are directed into the mass spectrometer inlet so that the chemical species in the eluates can be identified according to the ratios of the masses of the chemical species to the electric charges they carry.

To assist the desolvation of the ions before the ions enter the mass spectrometer, a high pressure gas called a sheath gas typically of research grade nitrogen or purified air is sometimes supplied axially and concentrically with the liquid flow so that the gas streams may strip away the water droplets or solvent molecules from the gas-phased solvated ions of interest resulting in enhanced sensitivity of the mass detection measurement. A high temperature created by heaters and other gases not axially directed as the liquid flow may also be applied to aid desolvation of the charged ions. If the molecules of interest are in a mixture, then high performance liquid chromatography (HPLC) is the most widespread technique used to separate the molecules in the mixture carried in a flowing liquid mobile phase based on their interactions with the stationary phase which is typically particles or other materials packed into a tube or capillary called a column. The spray emitter is connected to the exit end of the chromatographic column so that the eluates from the column can be vaporized and ionized with ESI for mass spectrometry analyses.

Mass spectrometry analyses of molecular species have advanced rapidly such that the detection limit of mass spectrometers can reach attomole ($10^{-18}$) level quite routinely when the flow rate of the liquid buffer is in the sub-microliter per minute or nanoflow regime. In this flow rate regime, the eluates can be vaporized and ionized under the applied electric field alone, i.e., no desolvation of ions using sheath gas or any other gases, or high temperature is needed. The resulting spray at this flow rate range is called nanospray, and the spray is characterized as a cone-jet mode since the spray appears to be drawn to a point slightly away from the spray emitter opening and burst into a cone-shape jet of fine mist carrying ions not requiring extensive desolvation before mass spectrometry detection. A popular spray emitter design in the art is made by melting the front end of a fused silica capillary with thermal energy either from a laser or a flame torch while pulling axially with a force so that the melted fused silica elongates and breaks, forming a taper with a small opening. For example, a fused silica capillary with an inside diameter of 75 μm and an outside diameter of 360 μm may be pulled to a taper over a few mm to about 1 cm to form an opening at the end that is a few μm to under 20 μm in diameter with an outside diameter that may be from about 10 μm to about 100 μm. The capillary which has a uniform inside diameter before pulling now has a gradually narrowing inside diameter in the tapered region. The taper opening generally creates a good spray, but the taper opening may change shape or may be damaged when used for nanospray operation over a period of time ranging from a few minutes to a few weeks. The spray tips with an opening of smaller than 10 μm in diameter may be prone to clogging and are structural fragile. Furthermore, the elongated channel of diminishing diameters inside the taper is also conducive to clogging. Spray emitters in the sub-microliter/minute flow-rate range of other designs are not as widely used than the melt-pulled fused silica emitter because the spray quality is considered not as good or consistent. One such spray emitter design is made of a stainless-steel tubing or a fused silica capillary tapered only on the outside wall leaving the inside diameter of the tubing uniform in size. Still another spray emitter in the sub-microliter/minute flow rate regime is a plastic injection-molded nozzle with a conical channel for conducting the liquid buffer to the spray opening. Still another design is just a flat-cut thin-walled fused silica capillary 20-25 um in inside diameter and 90-100 um in outside diameter. This flat-cut fused silica capillary is typically used with sheath gas to assist spray even in the sub-microliter flow rate range because it does not produce the cone-jet mode of spray. This flat-cut fused silica emitter is extremely fragile to handle due to its small diameters, and the sensitivity of detection from this spray emitter is not nearly as good as those capable of cone-jet mode spray. In addition, all the spray emitters in the art, even if they are capable of cone-jet mode spray for one range of liquid buffer compositions, usually from pure aqueous to pure organic solvent with some minor additive ingredients, and at one polarity of the high spray voltage, are not necessarily good at a different liquid buffer composition or high voltage polarity. In particular, negative ion spray is considered challenging for all the nanospray emitters in the art.

For the higher flow rate regimes, e.g., from a few microliters/minute to more than one milliliter/minute, the spray emitters in the art are made of a blunt-ended. i.e., untapered, stainless steel tubing, and the vaporization and ionization are assisted by high pressure gas and high temperature heaters around the spray region and also along the liquid and gas flow paths directly behind the spray emitter opening. These spray emitters are not capable of the cone-jet mode spray and as a result, the ionization efficiencies of these flat-ended stainless-steel spray emitters are considered less than that of the spray emitters producing cone-jet mode sprays in the nanospray regime. The sensitivity of the mass spectrometer detection of the molecular species in the higher flow rate regimes would have been compromised if not for the fact that the concentration of the molecules of interest can be increased substantially in most high flow-rate applications since sample availability is typically not a limiting factor, contrary to applications in the nanospray regime which are focused on proteins and peptides. Because of environmental concerns, there is a strong desire especially in the pharmaceutical and biotech industries to reduce the use of large amounts of solvents in liquid chromatography-mass spectrometry analyses, especially those exceeding 1 mL/minute. At the same time there is a push to attain the high sensitivity detection that has been achievable only with nanospray mass spectrometry because of the more stringent requirements in applications such as toxicity screening. However, nanoliters/minute flow rates for mass spectrometry sample input are considered both not robust enough and also too slow from the standpoint of high throughput analysis because the fused silica spray emitters are too fragile, and the stainless steel and plastic spray emitters have not been established to spray reliably and consistently so that human intervention during analyses is required.

SUMMARY

The spray emitters to be disclosed herein possess a reduced interfacial force between the emitter surface and the liquid to be electrosprayed, especially when the liquid is water or very polar. The spray devices that have improved spray stability over the entire chromatography buffer composition range typically used in liquid chromatography of biological and biologically-derived molecules, are capable of forming the unassisted cone-jet mode spray for a flow-rate range from sub-microliter/minute to at least 30 microliters/min, and have the same spray quality when either a positive or negative high voltage is applied to generate the electric field for spraying. Each disclosed spray emitter has an opening, preferably circular in shape, at the end of a cylindrical fluidic channel with no internal taper, and the surfaces in contact with the emitter opening, i.e., the end face (e.g., annular shaped end face of the emitter body that defines the end of the body and surrounds the spray emitter opening) of the spray emitter opening, and the (inner) surface of the cylindrical fluidic channel immediately behind, and to about at least 0.5 mm distant from the spray emitter opening, herein the combination of the end face and inner surface of at least a portion of the fluid channel being referred to as the emitter surfaces, have a surface with a property of reduced interfacial interaction with the aqueous or polar liquid to be sprayed. In one instance, the disclosed device is metallic and the emitter surfaces have a surface roughness that is smooth to less than 5 microns. As one of skill in the art would appreciate surface roughness, often shortened to roughness, is a component of surface texture. It is most often quantified by the deviations in the direction of the normal vector of a real surface from its ideal form. If these deviations are large, the surface is rough; if they are small, the surface is smooth.

To obtain (reduced) surface roughness of the scale described here on a metallic surface, electroformed nickel and nickel alloys from a mandrel with surface roughness of less than 5 um, and preferably less than 2 um, are used to fabricate the disclosed devices. The disclosed spray emitters, when compared to stainless steel emitters with or without a taper on the outside walls of the emitter openings in the art, have reduced surface wettability by the aqueous component of the liquid buffer at the spray emitter opening. The reduced surface wettability leads to an easier and more consistent formation of a liquid tip at the spray emitter opening where the liquid is subjected to the applied electric field to form the cone-jet mode spray. It is well-known in the art that the voltage threshold for a cone-jet mode spray is inversely proportional to the surface tension of the liquid. The relatively pure form of electroformed nickel and nickel alloys also minimizes the chemical variability when compared to stainless steel that may affect the consistency of the formation of the liquid tip. The low surface roughness of the surfaces in the vicinity of the disclosed emitter further eliminates sharp points that may generate erratic high electric fields in areas that produce sprays in unwanted directions, thereby decreasing the amount of ions of interest going into the mass spectrometer for analysis. Another embodiment of the disclosed device is a metallic lining of a metal, such as, gold less than 100 angstroms in thickness at the vicinity of the emitter opening of the metallic emitter that imparts the property of chemical selectivity to the emitter surfaces. The surfaces that are inherently hydrophobic which include most plastics are also disclosed to facilitate cone-jet mode spray when made into the shapes that are suitable for conveying an electrically charged liquid toward the mass spectrometer opening. The hydrophobicity of an inherently hydrophobic surface becomes more hydrophobic when the surface roughness is increased. This disclosure also describes a plastic spray emitter device with a preferred roughened surface near the spray emitter opening which facilitates the cone-jet mode formation during spray.

This application also discloses a device where the liquid sample to be sprayed is placed as a droplet on a sufficiently hydrophobic surface or a surface with reduced hydrophilic interfacial forces. When an electric field is applied to this liquid droplet, the shape of the drop is deformed so that it forms a liquid tip which then produces the cone-jet mode spray of the sample into the mass spectrometer for analysis. The more hydrophobic or less hydrophilic surface may be contoured to create a slanted protrusion at a preferred location of the surface so that the liquid tip may be formed and directed at the entrance of the mass spectrometer according to the slanting angle of the protrusion. When a device is arranged in an array format, multiple samples can be loaded on to the device for high throughput operation. The two-dimensional format of this disclosed device also facilitates the placement of heterogeneous samples. For example, when one of more lysed cells and their contents immersed in a liquid buffer which can be subsequently replenished with buffers of varying compositions on the disclosed device, the cell content can be electrosprayed into the mass spectrometry for analysis.

BRIEF DESCRIPTION OF THE DRAWING FIGURES

The foregoing and other features of the exemplary embodiments will be more readily apparent from the following detailed description and drawings of illustrative embodiments that are not necessarily drawn to show exact likeness or necessarily to scale in which.

DETAILED DESCRIPTION OF CERTAIN EMBODIMENTS

Figure 1:
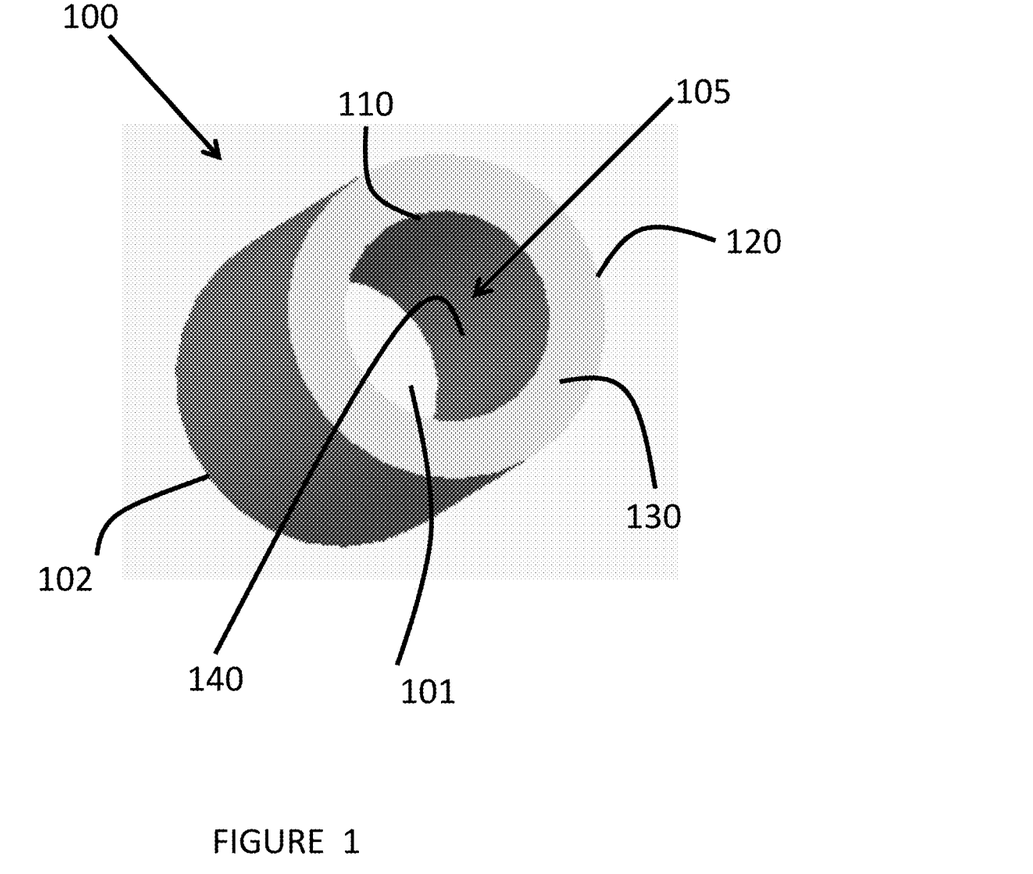
FIG. 1 is a perspective view of the disclosed spray emitter
Figure 2:
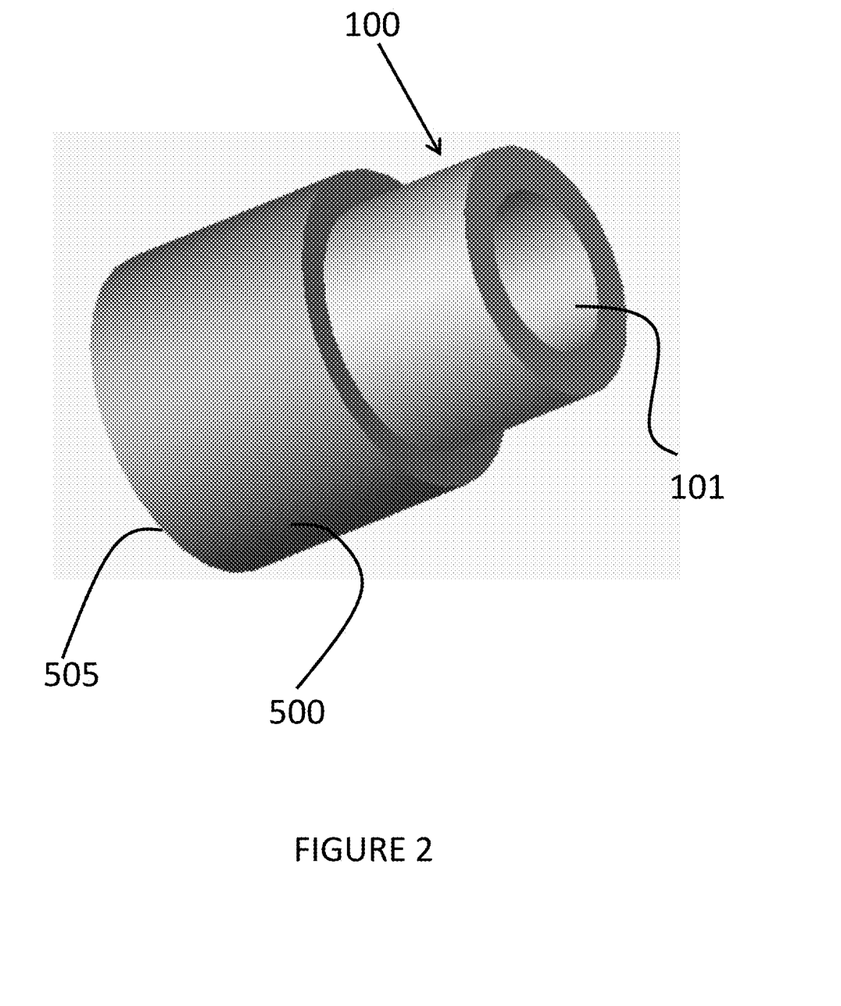
FIG. 2 is a perspective view of an embodiment of the disclosed spray emitter having a protective jacket around the spray emitter.
Figure 3:
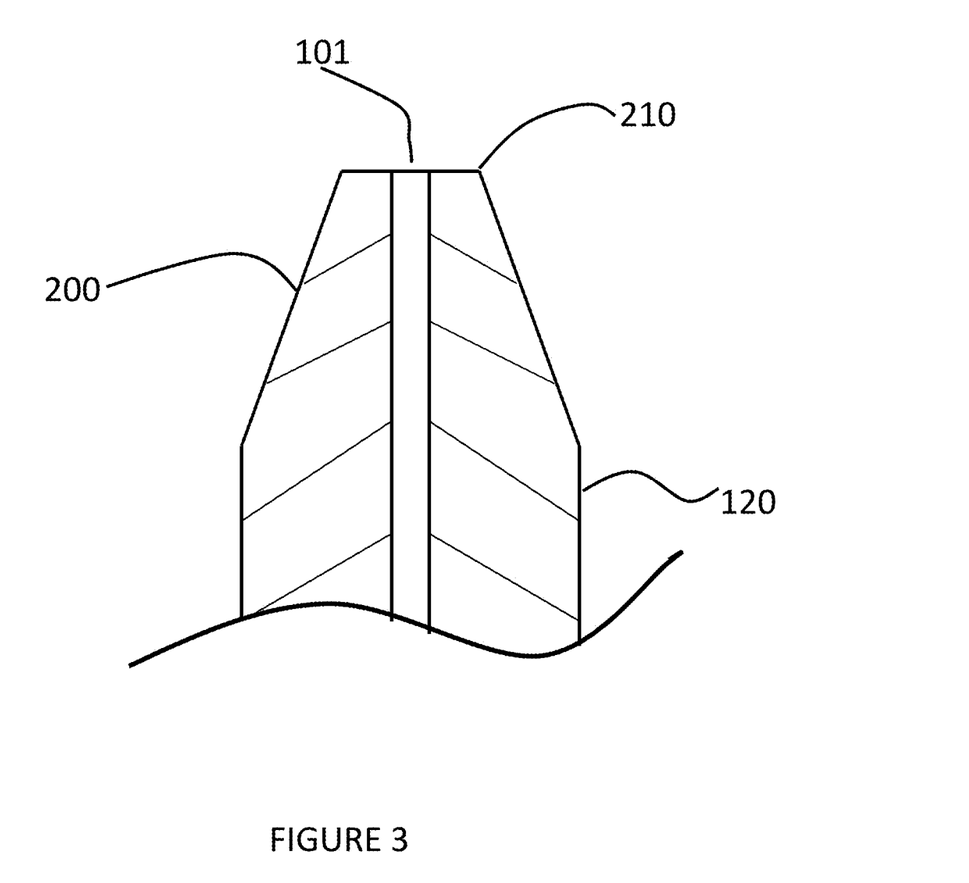
FIG. 3 is a cross sectional view of a spray emitter having a taper before the emitter opening so that the outer diameter of the spray emitter tube can be made larger for easier handling.

Referring to FIG. 1, the disclosed spray emitter is a metallic tubular form 100 which has an opening 101 at one end of a fluid-conveying channel 105 and also an opening at the distal end 102. The tubular form 100 has an inside diameter 110 of about 10 to 100 um with the preferred range of inside diameters from about 20 um to about 75 um; an outside diameter 120 having a range from about 30 um to about 100 um larger than the inside diameter, and the surface (an end surface) 130 at the face of the spray emitter opening 101, and the (inner) surface 140 of the fluidic channel 105 in the vicinity of the opening 101 having a surface roughness that is less than 5 microns, preferably less than 2 microns. In other words, a portion of the fluidic channel 105 has reduced surface roughness and this area is identified at character legend 140. The outside diameter 120 of the spray emitter opening 101 is preferred to be 150 um or smaller regardless of the size of the inner diameter 110. The portion of the reduced surface (surface 140) roughness fluidic channel should extend at least 0.5 mm from the spray emitter opening 101, and may be as long as the entire cylindrical fluidic channel itself. The length of the fluidic channel 105 and thus the tubular form 100 may be from a few millimeters to about 10 cm typical, but may be as long as 10's of cm in some applications. In the preferred embodiment of the invention, the spray emitter 100 is the opening of a capillary fabricated from electroformed nickel on a mandrel having a surface roughness of less than 5 micron, preferably less than 2 microns. It is well-known in the art that high purity nickel is chemically less active than stainless steel, which is a desirable property for a fluidic channel carrying biological and chemical molecules in a liquid buffer. Electroformed nickel and nickel alloys with copper and other metals are also known in the art to reproduce the surface of the mandrel to nanometer-scale accuracy, and diamond is known in the art as a suitable material that can be made into a mandrel with nanometer-scale surface roughness. The smoothness of the electroformed nickel surface reduces the hydrophilicity of the aqueous component of the liquid buffer inside the emitter opening 101 so that the liquid can be more easily and consistently drawn by the applied electric field to form a sharp liquid tip along the center line and a small distance, within one to two millimeters outside of the spray emitter opening 101. At a high enough applied electric field the liquid tip becomes unstable and bursts into a cone-jet mode spray.

In one embodiment of this disclosed device shown schematically in a perspective view in FIG. 2, a protective jacket 500 which may be made of a metal tubing such as a stainless steel tubing, or a polymeric material such as polyimide, polyether ether ketone (PEEK) and other suitable materials known to one skilled in the art and is coated onto or otherwise disposed on the outside diameter of the tubular form 100 from the distal end 102 to within a few millimeters of the spray emitter opening 101. The outside diameter 505 of the jacket should be made to sizes suitable for use with conventional liquid chromatography fittings. There are many instances of over coating of a polymeric material on a thin cylindrical structure such as an optical fiber or a fused silica capillary. The protective jacket 500 can be fabricated with similar processes. The protective jacket 500 is useful to ease handling of the spray emitter device 100 especially for those devices with an outside diameter of 100 um or smaller.

FIG. 3 shows the cross-sectional view of a spray emitter with the outside diameter of the electroformed nickel capillary made larger for the purpose of mechanical strength of the tubular form 100 for easier handling and connection to conventional liquid chromatographic plumbing fittings and the like. In this embodiment of the disclosed device, the outside diameter of the spray emitter opening is maintained to be about 30 um to about 100 um larger than the inside diameter of the spray emitter opening 101 by tapering the outside diameter of the capillary toward the spray emitter opening 101. The preferred outside diameter 210 of the tapered spray emitter opening 101 is 150 um or smaller. The taper 200 can be achieved during the electroforming process of the spray emitter form 100 on a mandrel having a taper. It may be more convenient from the electroforming manufacturing standpoint to obtain the taper 200 by mechanically and rotationally grinding one end of the cylindrical form 100 with polishing tools having grits of 10-20 microns or smaller so that the upper edge of the taper 200 closer to (proximate/adjacent) the emitter opening 101 has an average surface roughness of less than 5 um. The taper 200 may also be obtained by electrochemical etching and polishing up to a few millimeters of one end of the tubular form 100 containing the spray emitter opening 101 to obtain the inside diameters 110 and outside diameter 210 as described herein. To prevent the inside diameter of the spray emitter opening 101 from being etched larger, the tubular form 100 may be prefilled with distilled water and the distal end 102 of the fluidic channel 105 may be sealed with a plug or similar devices. The electrochemical etching process of nickel and the methods to prevent the inner diameter of a tube being etched are well known by one skilled in the art. The character legend 120 represents an outer diameter in a non-tapered area of the device.

In yet another embodiment of the disclosed device, the capillary body 100 in FIG. 1 is electroformed with an alloy of nickel and copper for applications with liquid buffers having a high salt content.

Figure 4:
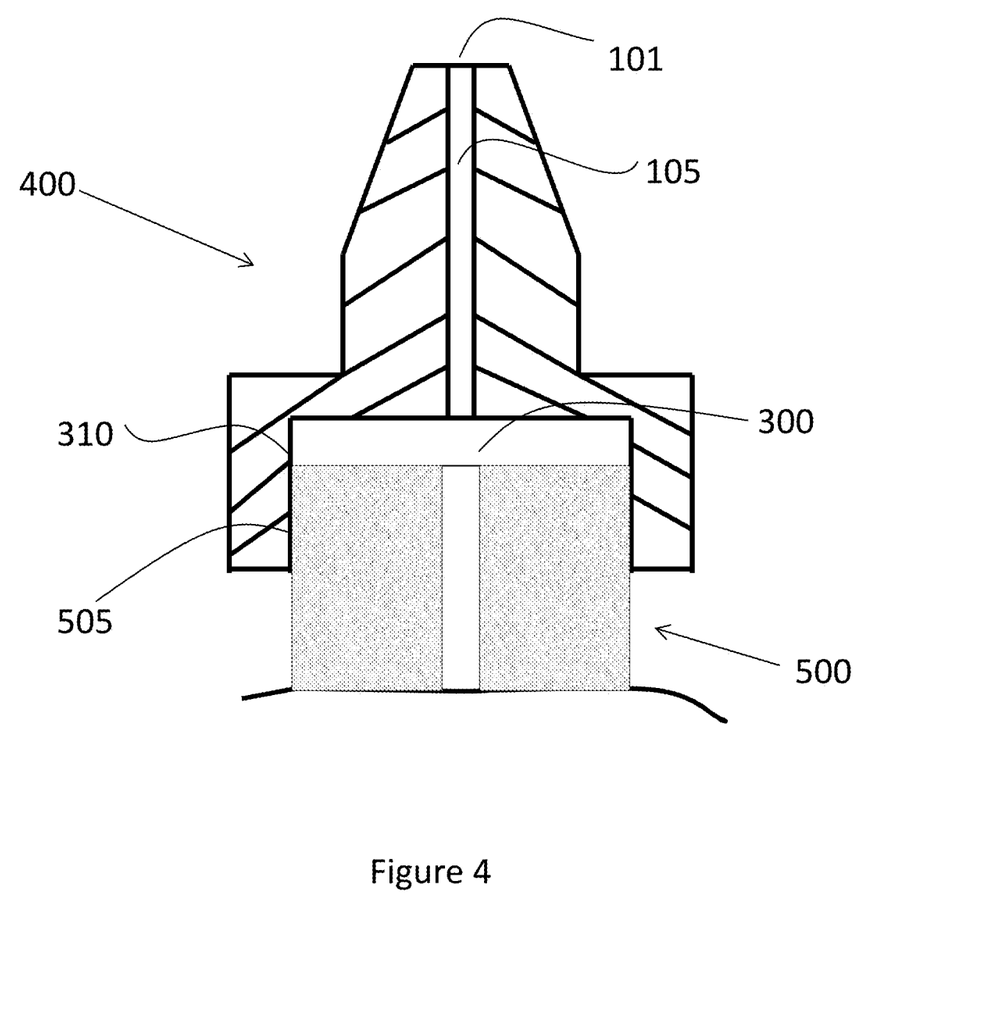
FIG. 4 is a cross-sectional view of a spray emitter having a fluidic channel of the same inside diameter as the spray emitter opening, which is connected and contiguous with a fluidic channel having a larger inside and outside diameters so that the larger channel can be connected in a liquid-tight fashion to an external tubing such as a chromatographic column without the use of fittings and with minimal dead volume in the connection. The schematic drawing shows the external tubing being partially inserted into the distal end of the spray emitter device.

Referring to FIG. 4, the spray emitter 101 of this disclosed device 400 may be situated at one end of a fluidic channel which has two distinct portions, a first portion 105 immediately behind the spray emitter opening 101, and a second portion 300 which has a larger inside diameter 310 until the distal end of the channel 300. The inside diameter 310 may be designed so that an external tubing 500 having an approximately the same outside diameter as the inside diameter 310 can fit in the inside diameter 310 of the fluidic channel 300 in a liquid tight fashion. The external tubing 500 is preferably a capillary column having a polymeric outside coating to facilitate the liquid-tight fit 505. In this configuration, the eluates from the capillary chromatographic column elute from the column directly into the fluidic channel 105 (e.g., into the first portion 105) and are sprayed by the spray emitter opening 101 with virtually no dead volume between the end of the capillary column 401 and the spray emitter 101 thus enhancing the sharpness of the chromatographic peaks. In this embodiment of the disclosed device, the device 400 is made by electroforming nickel on a similarly shaped diamond mandrel with a surface roughness of less than 5 um, and preferably less than 2 um. The device 400 may also be electroformed with nickel alloys with copper, chromium and the like.

As is known in the art, the devices as disclosed may be placed inside a concentric tube made of stainless steel, an inert plastic such as PEEK, or ceramic and glass, A gas from 1 to about 80 psi in pressure, preferably nitrogen or air in the purity grade suitable for mass spectrometry analyses, is supplied to flow through between the disclosed device and the outer concentric tube to create a sheath gas to help desolvation of the sprayed droplets.

Figure 5:
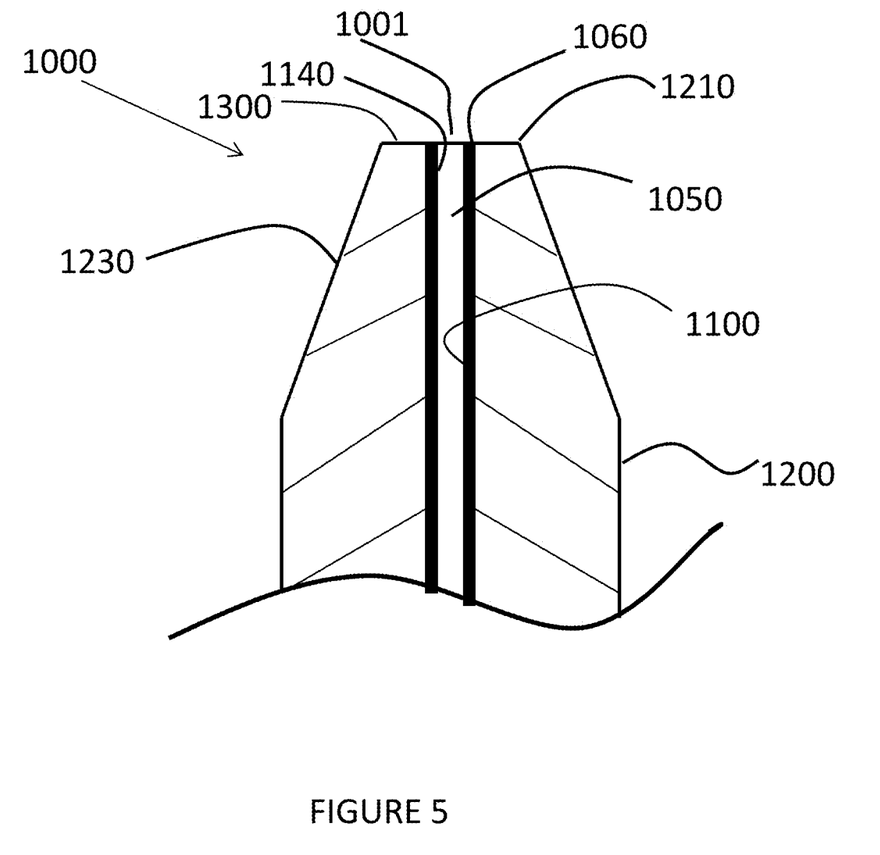
FIG. 5 is a cross sectional view of a metallic spray emitter with a metallic lining that enhances the chemical selectivity of the chemical species to be ionized and electrosprayed. The metallic spray emitter has an external taper before the emitter opening so that the outer diameter of the spray emitter tube can be made larger for easier handling.

Referring to FIG. 5, the disclosed spray emitter is a tubular form 1000 made of electroformed nickel which has an opening 1001 at one end of a fluid-conveying channel 1050 and also an opening at the distal end not shown. The tubular form 1000 has an inside diameter 1100 of about 10 to 100 um with the preferred range of inside diameters from about 20 um to about 75 um; an outside diameter 1200 having a range from about 30 um to about 100 um larger than the inside diameter, and the surface 1300 at the face of the spray emitter opening 1001, and the surface 1140 of the fluidic channel 1050 in the vicinity of the opening 1001 having a surface roughness that is less than 5 microns, preferably less than 2 microns. The outside diameter 1200 of the spray emitter opening 1001 is preferred to be 150 um or smaller regardless of the size of the inner diameter 1100. The portion (surface 140 that defines at least a portion of the channel) of the reduced surface roughness fluidic channel should extend at least 0.5 mm from the spray emitter opening 1001 toward the distal end of the fluidic channel 1050, and may be as long as the entire cylindrical fluidic channel itself. The length of the fluidic channel 1050 and thus the tubular form 1000 may be from a few millimeters to about 10 cm typical, but may be as long as 10's of cm in some applications. In the preferred embodiment of the invention, the fluidic channel 1050 of the spray emitter has a lining 1060 on the inside diameter extending from the emitter opening 1001 to at least 0.5 mm from the emitter opening and is made of a metal which is fabricated from electroforming on a mandrel having a surface roughness of less than 5 micron, preferably less than 2 microns. The thickness of the lining layer 1060 is made just enough to create a more or less continuous layer of the selected metal on the mandrel, preferably from about 20 angstroms to 100 angstroms. The lining 1060 has properties that aid in the optimization of the chemical selectivity of the species inside the liquid sample. In one embodiment of the disclosed device, electroformed gold is the material forming the lining 1060 because gold is considered among the most chemically inert material which is a desirable property for a fluidic channel carrying biological and chemical molecules in a liquid buffer. Gold is compatible with electroforming to reproduce the low surface roughness of the mandrel. Other materials which can be electroformed on a mandrel are also possible as the material for the lining 1060, e.g., alloys of nickel with copper, chromium, etc. The surface smoothness of the electroformed lining 1060 of the fluidic channel 1050 made of a variety of materials reduces the hydrophilicity of the aqueous and other organic but polar components of the liquid buffer inside the emitter opening 1001 so that the liquid can be more easily and consistently drawn by the applied electric field to form a sharp liquid tip along the center line of the spray emitter opening 1001, and at the same time, enhances the chemical selectivity of the chemical species available for ionization during electrospray. At a high enough applied electric field the liquid tip becomes unstable and bursts into a cone-jet mode spray.

In another embodiment of the disclosed device in FIG. 5, the lining 1060 made of gold in the thickness range of 20-50 angstrom is sputter-coated, evaporated or by any other suitable vapor deposition means onto the surfaces between the outside diameter 1210 of the taper 1100 and the inside surface of the fluidic channel 1050 within at least approximately 0.5 mm of the emitter opening.

Figure 6:
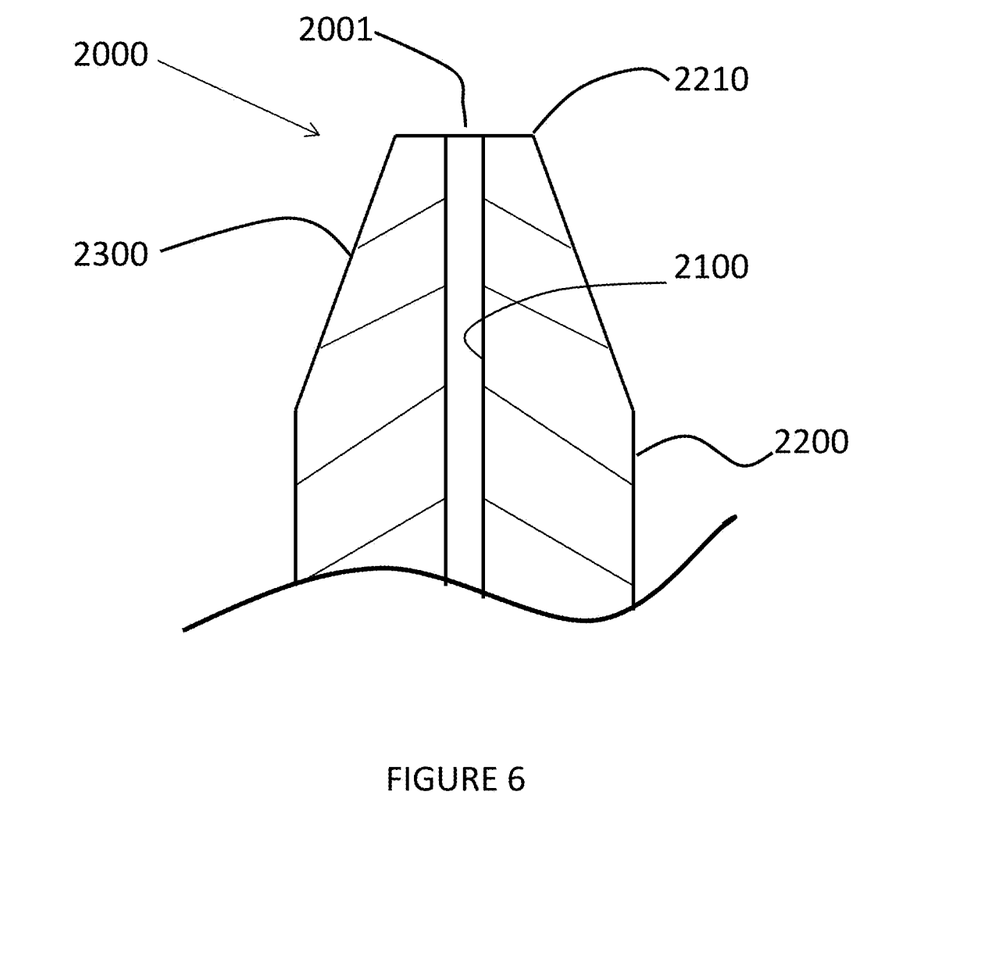
FIG. 6 is a schematic representation of a cross-sectional view of a plastic spray emitter having an external taper before the emitter opening so that the outer diameter of the emitter tube can be made larger for easier handling.

In a separate embodiment of the disclosed device, the spray emitter 2000 shown in FIG. 6 is made of a polymeric material such as polyether ether ketone (PEEK), polypropylene, high density polyethylene, a fluoropolymer such as Teflon®, FEP, PTFE, etc. The preferred form of the disclosed device in this embodiment is shown in FIG. 6 which shows the cross-sectional view of a spray emitter with the outside diameter made larger for the purpose of mechanical strength of the tubular form 2000 for easier handling and connection to conventional liquid chromatographic plumbing fittings and the like. In this embodiment of the disclosed device, the inside diameter of the fluidic channel 2100 is from about 10 um to about 100 um, with the preferred range from about 20 um to about 75 um; and the outside diameter 2210 of the spray emitter opening is maintained to be about 30 um to about 100 um larger than the inside diameter of the spray emitter opening 2001 by tapering the outside diameter of the capillary toward the spray emitter opening 2001. The preferred outside diameter 2210 of the tapered spray emitter opening is 150 um or smaller. The taper 2300 can be achieved in an plastic injection-molding process or an extrusion followed by injection molding, but the taper 2300 may also be obtained by mechanically and rotationally grinding one end of the cylindrical form 2000 with polishing tools having coarse grits of 50-100 microns followed by finer grits of 10 um to 50 um if desired so that the surfaces around the upper edge 2210 of the taper 2300 closer to the emitter opening 2001 have an average surface roughness of more than 10 um. For a hydrophobic surface such as a surface of a thermoplastic plastic, the hydrophobicity increases with the surface roughness so that the formation of a liquid tip from the liquid sample in contact with the roughened surface may be made easier. The liquid sample to be sprayed is charged with a high voltage before the liquid sample enters the all plastic spray emitter body 2000. To prevent static electricity charging of the outside surface of the body of the tubular form 2000, a very thin layer of gold of about 50 angstroms in thickness may be deposited on all the emitter surfaces of the tubular form 2000.

Figure 7:
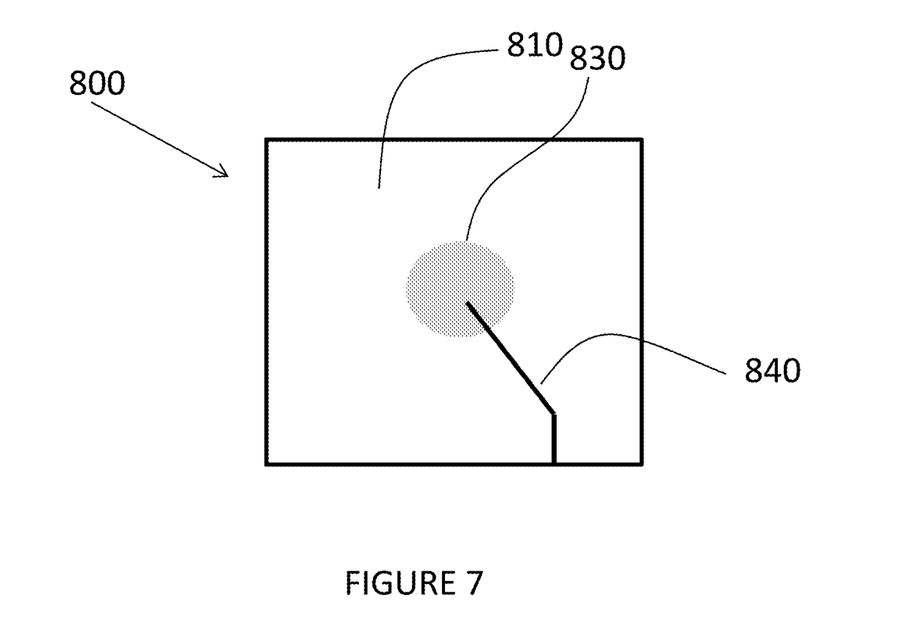
FIG. 7 is a two-dimensional device for electrospraying a microliter-scale droplet into the mass spectrometer for analysis.

In yet another embodiment of the disclosed device, the formation of the liquid tip by an applied electric field is created from a drop of liquid sample on a two-dimensional surface instead of from the opening of a cylindrical fluidic channel. Referring to FIG. 7, the device 800 comprises a mostly planar surface 810 made of a hydrophobic material such as a polymeric material which may be a medical device grade thermal plastic such as polypropylene, polycarbonate, high density polyethylene, polystyrene, polyether ether ketone (PEEK), a suitable fluoropolymer, etc. On the surface 810 is a sample deposition area 830. In one embodiment, the surface 830 may be roughened by sand blasting, grinding with sand paper having a fine grit of about 10 to 50 microns or any other methods known by one skilled in the art. The sample designation area 830 may be a small area up to a few mm$^2$ in diameter or it may be as large as the surface 810. In contact with the sample designation area 830 is an electrically conducting means 840 so that when a droplet of sample with a volume of about 1 microliter to up to about 5 microliters is placed on the sample contact surface 840, a high voltage or an electrical ground is in electrical contact with the sample droplet so that a high electric field customarily used to induce electrospray can be applied to the electrical conducting means 840 and an external electrode usually provided by the inlet of a mass spectrometer. The electrical conducting means 840 may be a patterned deposition or plating of a suitable conducting metal or a fine electrical wire. An electroformed nickel overlay electrode may be placed inside the sample designated area as the preferred electrical conducting means 840. For handling purposes, the device 800 may be a disc or a planar surface on top of a 3-dimensional object of any shape that is large enough to be handled by hand or by a robot. In one embodiment of the disclosed device, the device 900 comprises of an array of sample designated areas 930 and electrical conducting means 940 so that each sample designated area 930 is in contact with an electrical conducting means 940. A convenient array design for the device 900 is one compatible with the microtiter plate format of 96 or 384 sample deposition positions. Since the liquid samples to be deposited on the array of sample deposition areas are small droplets containing about 1 uL to a few uL in each sample designated area 930, some means to prevent the evaporation of the samples or to replenish the liquid sample while the samples are being sequentially sprayed into the mass spectrometer for analyses will be needed. A cover with one or more apertures which expose only the sample being sprayed to the electrode of the mass spectrometer inlet is desirable. The design of this cover and the robotic system that moves the device 900 so that each sample deposition area 930 remains under cover until it is moved to the spray position can be designed easily by one skilled in the art. A solid sample such as a lysated cell may also be deposited in the sample designated area 930 along with the liquid sample so that the cell content of the lysated cell can be analyzed when the liquid sample electrosprays into the mass spectrometer for analysis.

Figure 8:
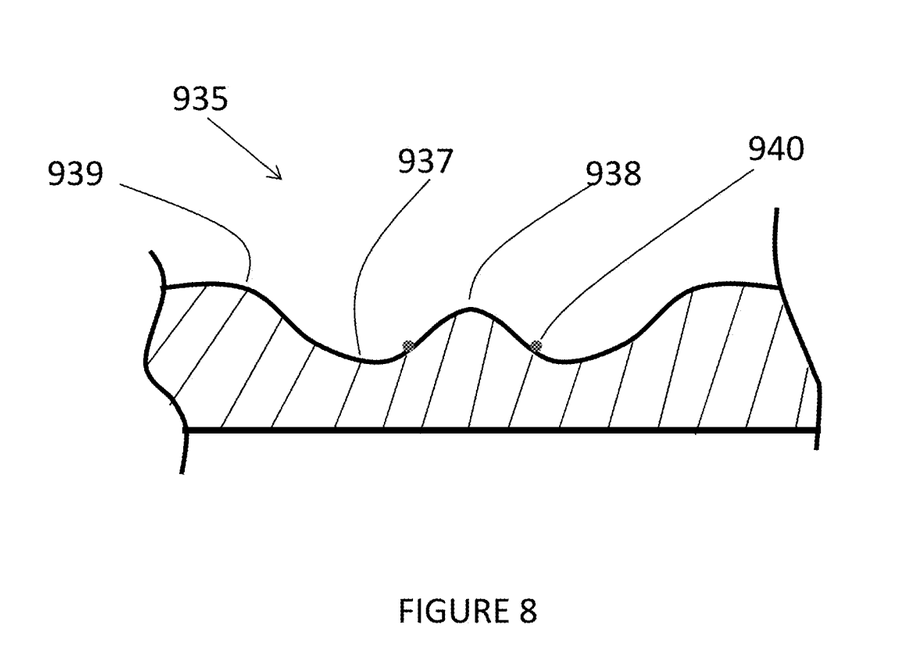
FIG. 8 is a cross sectional view of a sample designation area of an arrayed device showing a contoured surface in each sample designation area for facilitating the formation of the liquid tip and subsequent cone-jet mode spray under the influence of a large enough electric field.

In still another embodiment of the plastic device 900, the sample deposition area 935 may be contoured so that a larger amount of sample, e.g., even larger than 5 microliters, if applicable, may be deposited in a retention area but with a structure that aids the formation of the liquid tip. FIG. 8 shows an example of a cross-section of such a contoured sample deposition area 935 which has been roughened as described in this disclosure. The sample is deposited into this sample deposition area 935 which has a trough 937 around a slightly raised area 938 in the middle. The outer edge 939 of the trough 937 should be beveled and smooth and has an angle of larger than 90 degrees with respect to the wall of the trough. An electrical conducting means 940 is disposed within the sample deposition area 935. The sample volume should cover the raised area 938 but is below the trough's outer edge at the beginning of the spray. The liquid tip of the spray will be formed on the raised area 938 when a sufficiently large electric field is applied. Likewise, when a spray at an angle is required, the raised area 938 should be shaped to slant at the angle that the spray is directed. A cone-shaped spray results.

A method for depositing a series of drops of liquid buffer on the disclosed devices 800 and 900 having a varying organic and aqueous composition is also disclosed. When one of more lysed cells, or a mixture of biological and chemical species have been deposited on the areas 830 and 935 in devices 800 and 900, respectively, liquid droplets for electrospray having a varying organic and aqueous components depositing onto the deposited materials in a sequential manner extract appropriate parts of the lysed cell content or biological and chemical mixture into the liquid phase for electrospray and ionization for mass spectrometry analysis, as analogous to liquid chromatography in a column. The organic and aqueous composition of the droplets deposited sequentially may be of the kind that is used in gradient liquid chromatography well known in the art.

While the invention has been particularly shown and described with reference to preferred embodiments thereof, it will be understood by those skilled in the art that various changes in form and details may be made therein without departing from the spirit and scope of the invention.

EXAMPLE 1

An oligonucleotide with a molecular weight of about 6 kDa in 100% water was sprayed with the disclosed spray emitter electroformed from nickel on a diamond mandrel having a 50 um inside diameter, and 120 um outside diameter mechanically tapered from a 360 um outside diameter. The spray emitter opening was placed concentrically inside a stainless-steel sheath gas tube and protruded about 2 to 3 mm from the opening of the sheath gas tube. The liquid sample was pumped through the disclosed device with a syringe pump at 8 uL/minute. The applied voltage to induce spray was −2 KV. The mass of the triply-charge ion was detected with excellent signal to noise ratio on a Thermo OrbiTrap mass spectrometer tuned appropriately for this analyte. About 20 psi of research-grade nitrogen sheath gas was used to improve the signal in the mass spectrum, although a good signal of the ion was obtained without using any sheath gas. The concentration of the analyte was 2 ng/milliliter. Reducing the flow rate to 2 uL/min decreased the signal of the analyte ion but the signal was still steady, consistent and with good signal to noise ratio. This oligonucleotide had presented problems for detection using spray emitters in the art.

Utility

The disclosed spray emitter device is a clog-resistant device that improves the spray stability and the ionization efficiency of the liquid buffer carrying the molecular species of interest for mass spectrometry analyses in the flow-rate range below 10's of microliter/minute by enabling the cone-jet mode spray under a large variety of spray conditions with respect to the chemical compositions of the liquid buffers and the polarities of the applied electric field to induce spray. Some embodiments of the disclosed device improve the separation efficiency of liquid chromatography. In addition, static nanospray emitters that allow easy, convenient sample loading and high throughput operations are disclosed.

What is claimed is:

1. A spray emitter for spraying a fluid comprising:

an emitter body formed of a metal and having an inner channel formed therein that terminates at a spray emitter opening at a first end of the emitter body, wherein the inner channel is defined by an inner wall surface of the emitter body, the inner wall surface having a first portion that extends to the spray emitter opening, wherein the emitter body includes an end face that surrounds the fluid emitter opening at the first end of the emitter body, wherein the end face and the first portion define emitter surfaces that have a reduced surface roughness for reducing interfacial interaction with the fluid, the reduced surface roughness being a surface roughness less than 5 microns.

2. The spray emitter of claim 1, wherein the reduced surface roughness is less than 2 microns.

3. The spray emitter of claim 1, wherein the first portion extend in a longitudinal direction within the inner channel and extends at least about 0.5 mm from the spray emitter opening.

4. The spray emitter of claim 1, wherein the emitter body has a cylindrical shape and is open at the first end and an opposite second end.

5. The spray emitter of claim 1, further including a protective jacket that is disposed about and coupled to the emitter body, the first end of the emitter body extending beyond a free end of the protective jacket, the protective jacket comprising one of a metal tube and a plastic tube.

6. The spray emitter of claim 1, wherein the emitter body comprises a tube having an inner diameter between about 10 microns and about 100 microns and an outer diameter that is between about 30 microns and about 100 microns greater than the inner diameter.

7. The spray emitter of claim 1, wherein the emitter body is formed of electroformed nickel.

8. The spray emitter of claim 1, wherein the emitter body has a tapered portion that terminates at the first end of the emitter body, wherein a second end of the emitter body has a uniform outer diameter, wherein a distal end section of the tapered portion has a reduced surface roughness of less than 5 microns.

9. The spray emitter of claim 1, wherein the emitter body has a first portion that terminates at the first end and a second portion that terminates at a second end, the second portion having an outer diameter that is greater than an outer diameter of the first portion, the second portion having a hollow space that is in fluid communication with the inner channel, the hollow space being configured to receive a tube for delivering the fluid to the inner channel, the inner space having an inner diameter greater than an inner diameter of the inner channel.

10. The spray emitter of claim 1, wherein the inner channel has a liner that is formed on an inner wall that defines the inner channel, the liner extending from the spray emitter opening to a point that is at least about 0.5 mm from the spray emitter opening.

11. The spray emitter of claim 10, wherein the lining is formed of an electroformed alloy of nickel and copper.

12. The spray emitter of claim 1, wherein the end face has an annular shape.

13. A spray emitter for spraying a fluid comprising:

an emitter body having an inner channel formed therein that terminates at a spray emitter opening at a first end of the emitter body, wherein the inner channel is defined by an inner wall surface of the emitter body, the inner wall surface having a first portion that extends to the spray emitter opening, wherein the emitter body includes an end face that surrounds the fluid emitter opening at the first end of the emitter body, wherein the end face and the first portion define emitter surfaces; and a coating formed on the emitter surfaces, the coating being formed of gold and having a thickness of less than 50 angstroms.

14. The spray emitter of claim 13, wherein prior to coating the emitter surfaces, the emitter surfaces are processed to provide a reduced surface roughness of less than 5 microns.

15. The spray emitter of claim 13, wherein the first portion extend in a longitudinal direction within the inner channel and extends at least about 0.5 mm from the spray emitter opening.

16. The spray emitter of claim 13, wherein the end face has an annular shape.

17. A spray emitter for spraying a fluid comprising:

an emitter body formed of a plastic and including a contoured upper surface that has a sample deposition area, the sample deposition area being defined by a trough so as to permit the fluid to be contained within the trough; and an electrical conducting device disposed within the sample deposition area and configured to form a liquid tip of a spray when an electric field of between 1 KV and 5 KV is applied to the electrical conductive device.

18. The spray emitter of claim 17, wherein the sample deposition area has an increased surface roughness, the trough having a raised middle area to divide the trough into first and second concave trough sections, the trough being defined by outer edges that are disposed above a top of the raised middle area so as to permit the fluid to be contained within the trough so as to cover the raised middle area; and the electrical conducting device disposed being configured to form on the raised middle area a liquid tip of a spray when the sufficient electric field is applied to electrical conductive device.

19. The spray emitter of claim 18, wherein the electrical conductive device comprises a first conductive path formed on one side of the raised middle area and a second conductive path formed on an opposite side of the raised middle area.

20. The spray emitter of claim 17, wherein the emitter forms an ordered array for high throughput operation.

* * * * *